(12) United States Patent
Feichtinger

(10) Patent No.: US 6,849,230 B1
(45) Date of Patent: Feb. 1, 2005

(54) MIXTURE OF TWO PARTICULATE PHASES USED IN THE PRODUCTION OF A GREEN COMPACT THAT CAN BE SINTERED AT HIGHER TEMPERATURES

(75) Inventor: Heinrich Feichtinger, Zürich (CH)

(73) Assignee: Stratec Medical AG, Oberdorf (CH)

( * ) Notice: Subject to any disclaimer, the term of this patent is extended or adjusted under 35 U.S.C. 154(b) by 0 days.

(21) Appl. No.: 10/088,056

(22) PCT Filed: Sep. 14, 1999

(86) PCT No.: PCT/CH99/00434

§ 371 (c)(1),
(2), (4) Date: Jul. 16, 2002

(87) PCT Pub. No.: WO01/19556

PCT Pub. Date: Mar. 22, 2001

(51) Int. Cl.$^7$ ............................................... C22C 14/00
(52) U.S. Cl. .......................... 420/417; 419/36; 419/37; 419/38
(58) Field of Search ........................... 420/417; 419/36, 419/37, 38

(56) References Cited

U.S. PATENT DOCUMENTS

| 3,852,045 A | 12/1974 | Wheeler et al. |
| 4,517,069 A | 5/1985 | Harney et al. |
| 5,034,186 A | 7/1991 | Shimamune et al. |
| 5,520,879 A * | 5/1996 | Saito et al. ................... 419/38 |

FOREIGN PATENT DOCUMENTS

| DE | 2 256 716 A | 6/1974 |
| DE | 197 25 210 C | 11/1998 |

* cited by examiner

Primary Examiner—Daniel Jenkins
(74) Attorney, Agent, or Firm—Rankin, Hill, Porter & Clark LLP

(57) ABSTRACT

A mixture of two particulate phases used in the production of a green compact that can be sintered at higher temperatures. The first phase contains particles that consist of a metal and/or a metal allow and/or a metal compound. The second phase contains particles from the group of the inorganic compounds that do not release any decomposition products at temperatures of more than 400° C., that are interstitially soluble in the sintering metal phase, and/or that react with the second phase to stable compounds. The mixture, by providing the second phase, is effective in supporting the fine structure of the first phase against the forces of surface tensions during the sintering process. During sintering, the second phase remains thermally stable and substantially chemically inert with respect to the first phase.

22 Claims, No Drawings

MIXTURE OF TWO PARTICULATE PHASES USED IN THE PRODUCTION OF A GREEN COMPACT THAT CAN BE SINTERED AT HIGHER TEMPERATURES

The invention relates to a mixture as claimed in the precharacterising part of claim 1, a method for producing said mixture, and applications thereof.

Metallic structures with interconnecting pores, particularly if containing higher pore volumes and, consequently, extremely thin cell walls, present the problem, due to their high specific surface area, of being subject to an intense sintering activity. If a structure of this type, originally consisting of smaller metal particles, is to be sintered to a sufficiently solid and dense, shaped body, this will generally, for three-dimensionally extending phases, necessitate temperatures of at least about 75 to 80 percent of the melting temperature. This temperature must be selected because the volume diffusion necessary for the redensification of the sintered structure would not take place quick enough at lower temperatures. However, a metal structure with interconnecting pores characterised by a high degree of porosity consists to a great extent of internal surface areas, and, therefore, its sintering behaviour throughout the entire sintering process is largely characterised by surface diffusion, which requires a considerably lower thermal activation. The application of the above-mentioned sintering temperatures, which are normally necessary for producing a dense, metallic structure, will thus inevitably result in a reduction of the internal surface area. Due to the effect of the surface tension, a more or less significant shrinkage of the shaped body will occur, which, on the one hand, has a negative influence on the overall dimensions of the body and, on the other hand, leads to a reduction in pore volume. This process may be avoided by reducing the sintering temperature to lower values, which correspond to the thermal activation necessary for surface diffusion to take place. Although it is possible, in doing so, to largely maintain the macrogeometry of the shaped body, only thin sintering necks are formed between adjacent metal particles and the shaped body thus presents only an insufficient strength. The effect described above makes it practically impossible for fine-structured, shaped bodies with interconnecting pores having cell walls in the range of a few micrometers and pore diameters of less than 0.5 mm to be exposed to a normal sintering process: the surface tension acting as a driving force will cause the pores initially present in the green compact to become smaller and smaller while the cell walls are getting thicker and thicker.

In metallurgical and ceramic technology, numerous methods for producing shaped bodies with interconnecting pores are known. The simplest method consists in using an appropriate binder to compress a loosely arranged mass of particles so as to form a shaped body and to sinter this shaped body subsequently. If in doing so the density is inferior to 95 percent of the theoretical value, the body will automatically have interconnecting pores. Bodies fabricated in this way, such as those typically produced for self-lubricating bearings, however, consist of a pore network displaying the negative image of the metal particles by which it is surrounded. Said network consists of narrow, sharp-edged pore channels and as the cohesion of the particles must be assured by means of the contact surfaces existing between them, it is not possible to achieve porosity rates which are considerably higher than 50 percent by volume. For this reason, this type of manufacturing has to be ruled out a priori for numerous functional applications, for example in the field of medical implants.

In ceramic sintering technology, for example in the production of abrasive disks, particles of a second phase, together with a binder, are frequently added to the mixture and, subsequent to sintering, eliminated again therefrom at lower temperatures, leaving behind a network of cavities. To this end, naphthalene balls may, for example, be added to the abrasive particles before the sintering process. These balls provide a hollow volume about which the finer particles of the ceramic phase are arranged. As the naphthalene balls vaporize at temperatures below 100 DEG C, the only function of the balls is to provide pore volume in the green compact and the subsequent sintering process must be conducted in such a way that the specified dimensional limits for the abrasive disk are respected, which requires a high degree of empirical experience, as far as the adequate choice of processing duration and temperature is concerned.

In cases in which the composition of a porous, metallic, shaped body includes the use of binders for making up a green compact, it must be possible to eliminate these binders under reducing and/or neutral atmospheric conditions at very low temperatures, thus excluding any risk of an absorption of binder components by the metallic matrix, because unlike in ceramic systems oxidizing burning out is generally not practicable. Such binder systems are usually selected from the group of organic compounds and may be eliminated from the sintered compact practically without leaving a trace at temperatures below 200 to 400 DEG C through degradation and/or vaporization. They include thermoplastic binders, for example paraffins or waxes, partially mixed with polymers such as PE, PP and with further additives as for example carboxylic acid and its esters, thermosetting binders, e.g. furan resins, or gel binders such as aqueous solutions of methyl cellulose.

Conventionally, sintering processes are primarily used in order to obtain a metallic body which is as dense as possible. For this reason, the elimination of the binder phase already at very low temperatures is of no importance, or rather, on the contrary, is even a prerequisite for obtaining the highest possible density. For the normal process, it is perfectly sufficient that the binderless green compact keeps merely a rudimentary density so as to maintain its shape. However, if a structure with interconnecting pores and above all with thin cell walls is to be realised, an early elimination of the binder and of the pore-forming phase supporting the structure turns out to be of great disadvantage. The pore structure is now exposed without protection to the forces of surface tension, and the shaped body begins to shrink, the cell walls becoming thicker and thicker and the channels between the interconnecting pores being increasingly closed. Here, the definite geometry of the shaped body is a function of the local pore geometry (radius of curvature) as well as of processing time and temperature and, therefore, cannot be controlled with precision.

U.S. Pat. No. 5,034,186 SHIMAMUNE ET ALII discloses a method according to which a highly porous surface layer is produced on a titanium-based electrode by mixing a fine-particle titanium powder with up to 75 percent by volume of a magnesium powder. Unlike thermally unstable, organic pore forming materials, the magnesium particles remain in the mixture at higher temperatures and exert a stabilizing influence, but, at the same time, produce magnesium vapour which due to its high reactivity may react with e.g. oxidic or nitrogenous decomposition products that occur during the sintering of the first metal phase, said reaction resulting in the formation of magnesium oxide or magnesium nitride, which leads to a strong expansion of the pore cavities, which may, eventually, give rise to microcracking.

The invention is intended to provide a remedy for all the disadvantages mentioned above and is in particular effective in supporting the fine structure of the first phase against the forces of surface tension occurring during the sintering process by providing a second phase which during the sintering process remains thermally stable and substantially chemically inert with respect to the first phase.

According to the invention, this object is achieved by means of a mixture of two particulate phases according to the features of claim 1 which form a green compact that can be sintered at higher temperatures, wherein A) the first phase contains particles that consist of a metal and/or a metal alloy and/or a metal compound; and B) the second phase contains particles, selected from the group of the inorganic compounds which at temperatures beyond 400 DEG C do not release any decomposition products that are interstitially soluble in the sintering metal phase and/or react with said phase to form stable compounds.

In accordance with claim 1, it is thus an important characteristic of the particles of the second phase, designed to provide a volume of empty spaces of a desired geometry within the mixture, that, on the one hand, they belong to the group of inorganic compounds, generally provided with a considerably higher thermal stability, and, on the other hand, said inorganic compounds do not release any decomposition products which either dissolve interstitially in the sintering metal phase or react with said phase to form stable compounds. In both cases this will generally lead to an embrittlement of the metal phase. According to a preferred embodiment of the invention, a releasing of these detrimental elements is prevented in so far as either the bonds by which these potentially dangerous elements are contained in the second phase are so strong that at the sintering temperature they are not set free for interaction with the metal phase, or the halogenides of the alkali metals or the alkaline earth metals are selected as inorganic compounds, which, on the one hand, have high melting and evaporating temperatures and, on the other hand, do not contain said detrimental elements. Incidentally, since in metallurgy there are no systems known which are not, at least in infinitesimal proportions, liable to thermal disintegration, the expression "are not set free for interaction with the metal phase" is to be understood as meaning that the amounts set free are so small that the mechanical properties of the metal phase are not negatively influenced by them.

The elements interstitially soluble in a metal phase include carbon, oxygen, nitrogen, sulphur, and phosphorus.

It is, however, permissible for the sintering of titanium structures to use for example calcium oxide as a second phase, since the bonds by which the oxygen is contained in calcium oxide are so strong that the titanium is not capable of deoxygenising the second phase, which would lead to an embrittlement.

According to a preferred embodiment of the invention, sodium chloride, calcium fluoride as well as cryolites are used to compose the second phase.

The particles of the first phase may contain metals and their alloys as well as metal compounds. If metal compounds are used, preference is given, according to a preferred embodiment of the invention, to thermally unstable oxides, nitrides or hydrides which when exposed to sintering are decomposed into their respective metals. The selection of hydrides is in so far of particular interest as on the one hand they are thermally unstable and therefore disintegrate relatively easily, whereas, on the other hand, their decomposition product is hydrogen, a reducing gas which, due to its high rate of diffusion—provided the hydrogen potential of the environment is sufficiently low, for example through the action of a vacuum or an inert gas—may rapidly be eliminated from the sintering metal phase.

In a preferred embodiment of the invention, the first phase consists of titanium or titanium alloys and/or titanium hydride. The alkali halogenides or the alkaline earth halogenides are particularly suitable materials for composing the second phase, as these compounds do not contain carbon, nitrogen, or oxygen, generally known to be readily absorbed by titanium, which in doing so looses a great deal of its tenacity. These halogenides are known, in part, for playing a role in the normal production process of titanium. Magnesium chloride, for example, occurs in Kroll's process as a chemically inert by-product of the reaction between titanium chloride and magnesium, along with titanium sponge, the principle product of this reaction; or in another reduction process sodium iodide results along with titanium as a decomposition product of titanium iodide.

As far as their geometry and their composition are concerned, the two phases of the mixture which make up the shaped body may immediately consist of the particles of the two phases that are mixed together (in this case the term "particle" refers actually to the corresponding powder particles that compose the respective phases). However, it is also possible that prior to being mixed with the other phase, the powder particles of one phase are shaped into simple agglomerates, such as balls or even more complex geometrical structures, by means of a suitable binder, before allowing said particles to become mixed with the particles of the other phase, the powder particles of which may, for example, equally have been previously agglomerated. If the composition of the particles of one phase includes a binder which would give off detrimental decomposition products to the metal phase during the sintering process, it must be possible to eliminate said binder at temperatures below those at which the sintering process starts—as is the case for binder systems used on a superior level for binding the two phases. Generally, organic binder phases such as those described above in connection with the injection moulding process are used for this purpose.

As stated above, the principle object of the method according to the invention is to obtain a rigid, metallic cell structure while maintaining the inner surface areas and volumes. This object is primarily achieved by the fact that the second phase, designed to provide a volume of empty spaces, continues to exert its supporting action even after the sintering temperature has been reached. Generally, the efficiency of this process can be said to turn out the better the lower the temperatures are at which the sintering process leads to a dense cell structure. This may be realised, in accordance with claim one, by using easily decomposable metal compounds in addition to the metal powders to form the first phase. In the sintering technique of titanium powders, titanium hydride is sometimes used as a sintering adjuvant. Whereas normal titanium powders necessitate temperatures in a range of between 1,200 and 1,300 DEG C for a dense sintering process to take place, fine-grained titanium hydride powders disintegrate already at temperatures over 600 DEG C, depending on the hydrogen partial pressure of the environment, and the sintering process of the nascent titanium may start at temperatures as low as below 800 DEG C.

This early sintering process may be further encouraged by selecting suitable alloys and using the technology of liquid phase sintering. According to a preferred embodiment of the invention, at least part of the particles forming the first phase, i.e. metals, metal alloys or metal compounds, may be coated, by means of any known coating process, with a low-temperature melting alloying element, said element being present after the sintering process in the correct concentration for the desired alloy. A particularly elegant way of using this procedure is to apply an aluminium coating on titanium particles or titanium hydride particles previously alloyed with vanadin in order to produce a structure consisting of the known alloy Ti6Al4V. As a temperature of 660 DEG C is reached, a liquid aluminium phase is formed which, due to the interfacial surface tension, contracts on the points of contact with the metal particles. As the temperature is further increased, more and more alloying elements are introduced among the titanium particles, resulting rapidly in the formation of a strong bonding between the particles of the first phase.

It is advisable to have only part of the particles coated.

As with smaller particles even thin coating thicknesses may lead to too great an increase in concentration on the respective element, it may be advisable to coat for example only 10 percent of the particles, so as to obtain a thinner coating thickness. The experiment of producing a titanium alloy containing 6 percent of titanium would, for example, result in the formation of extremely thin-layered aluminium coatings.

According to a preferred embodiment of the invention, the production of shaped bodies may also be realised without the addition of a binder by using a loose powder sintering technique which consists in filling the well-mixed particles of the first and second phases, using, if necessary, a compacting means such as a vibrator, into a mould which is thermally and chemically stable at the sintering temperature. In the case of a chemically highly reactive metal phase, such as titanium or its alloys, generally known to attack most ceramic moulds, said mould may alternatively consist of one of the materials to be used, according to claim 4, for the second phase, for example sodium chloride. A mould of this type made of sodium chloride is stable up to a temperature of 801 DEG C. Said mould will melt only beyond this temperature, as do the salt particles present within the shaped body, said shaped body thus exposed from within and without having undergone enough presintering at this temperature so as to have reached a sufficient degree of inherent stability. It goes without saying that for the treatment of less reactive metals said loose powder sintering process may also be carried out using permanent moulds made of ceramic or metal. If the permanent mould used is made of metal, its surface must be adequately smoothed in order to avoid the occurrence of diffusion weldings.

According to a preferred embodiment of the invention, the shaped body consisting of the first and second phases may also be formed into a green compact and stabilized by means of a third binder phase which, by analogy with powder injection moulding, is eliminated from the shaped body prior to the beginning of the sintering process, properly speaking, by means of decomposition and/or evaporation, leaving behind a shaped body with a sufficient degree of green strength. Unlike in powder injection moulding, where this binder phase fills up the space between the metal particles to a high degree in order to achieve advantageous rheological properties, thus necessitating a prolonged and difficult dewaxing process, the binder phase of the method according to the invention may in many cases be used in a considerably lower concentration, since it only has the function of assuring that the particles of the two phases stick together on their points of contact, so that a shaped body with sufficient rigidity is created. The degassing process of the binder is facilitated by the presence of sufficiently dimensioned channels permitting said process to take place in a simple and rapid manner. Its duration merely depends on the minimum time which is necessary for the shaped body to obtain a sufficient degree of green strength. However, if the injection moulding process is used for the production of shaped bodies, the binder is subject, in terms of quantity, to the usual conditions required for obtaining a sufficient injectability in the injection moulding machine. In this case the dewaxing process will then of course be slowed down correspondingly.

In the following, the method according to the invention will be described with reference to several embodiments.

EXAMPLE 1

A first example describes the production of a metal structure with interconnecting pores shaped in the form of a cylinder made of stainless steel, having a diameter of 20 mm and a length of 80 mm. For this purpose, a steel powder with a percentage composition of about 18 percent by mass of chromium and 9 percent by mass of nickel having a medium particle size of 20 $\mu$m was mixed with 80 percent by volume of approximately ball-shaped calcium carbonate particles having a medium diameter of 0.2 mm, adding 2 percent by mass of an organic paraffin, and compressed in a mould so as to form shaped bodies. The shaped bodies were subsequently placed in a protective atmosphere furnace and subjected to the following temperature programme:

| 3 h | 25–300 DEG C. | flowing argon |
|---|---|---|
| 3 h | 300–1,100 DEG C. | flowing forming gas (93% argon, 7% hydrogen) |
| 6 h | 1,100 DEG C. | flowing forming gas |

At a temperature range of 900 DEG C, the calcium carbonate was decomposed into burnt lime, with delivery of carbonic acid. This process was accompanied by only a slight shrinkage of the calcium oxide particles, the substantial volume shrinkage being due to the formation of very fine pore channels in the calcium oxide particles. For this reason, only a very slight diameter and length reduction of the cylinder as compared to the initial state was observed. After termination of the sintering process, the sintered sample body was cooled down and removed from the furnace. The shaped body was subsequently immersed for several days into a strongly diluted and briskly stirred hydrochloric acid, whereupon the calcium oxide was completely hydrated and thus eliminated from the shaped body. The result was a highly rigid, high-tenacity shaped body having a relative density of 32 percent, referred to the density of stainless steel.

EXAMPLE 2

A second example describes the production of an interconnecting pore structure in the form of a stainless steel filter having a height of 8 mm and a G1/8" external screw thread, the pore size, however, being smaller almost by the power of ten than that of the preceding example. Since the filter is required to have regular, spheroidally convex cavities with pore diameters of maximally 35 $\mu$m, it would be necessary to use metal particles with particle sizes of less than 500 nm, for only powders of this fineness are capable of constituting the thin cell walls around the volume forming phase, which in the present example consisted equally of calcium carbonate particles having a medium diameter of 30 $\mu$m. Such stainless steel powders, however, are not commercially available, and their production would be extremely expensive. For this reason, a mixture of iron oxide, chromium oxide and nickel oxide stoichiometrically corresponding to the alloy was used, with the medium particle size of all particles being inferior to 500 nm. This powder constituting the first phase was homogeneously mixed with the calcium carbonate balls without adding a binder and subsequently filled into a thin-walled alumina mould. This mould had previously been fabricated using the lost-wax process by investment casting of a corresponding wax pattern. This mould was placed in a protective atmosphere furnace and subsequently subjected to the following time-temperature programme:

| | | |
|---|---|---|
| 5 h | 25–1,350 DEG C. | flowing, pulsating, technical hydrogen |
| 3 h | 1,350 DEG C. | flowing, pulsating, high-purity hydrogen |

In order to ensure that the reduction process of the oxides took place under favourable kinetic conditions, the hydrogen pressure, which normally was 1,050 mbar, was increased for 10 seconds to 1,500 mbar every 2 minutes. By this measure, the steam formed during the reduction process was rarefied and fresh hydrogen was continually allowed to reach the inner surface areas of the shaped body. After cooling down, the shaped body was removed from the furnace and washed in diluted acid. Due to the fact that the reduction of metal oxides implies a considerable decrease in volume and that, on the other hand, the calcium oxide particles largely maintained their external shape, this resulted not so much in a shrinkage of the shaped body as such but rather led to an increase in its degree of porosity, as the contact points had a smaller diameter due to the strong shrinkage which had occurred during the reduction process. The grinding pattern of the structure showed an austenitic matrix largely free of non-metallic inclusions, which was equally confirmed by the good tenacity properties of the shaped body.

EXAMPLE 3

A third example describes the fabrication of a medical implant for the head of a hip prosthesis made of pure titanium. For this purpose, a mixture consisting of 60.7 percent by mass of sodium chloride balls which had previously been screened out to a diameter of between 0.6 and 0.85 mm was mixed with 21.3 percent by mass of titanium hydride particles having a particle size of between 1 and 3 $\mu$m, adding 18 percent of a saturated, aqueous sodium chloride solution containing 5 percent of isopropyl alcohol, so as to form a homogeneous paste. This paste was inserted under vibration into a metal-reinforced, two-piece silicone rubber mould and subsequently dried during 24 hours in a drying cabinet at 80 DEG C. The demolded body was subsequently placed in a protective atmosphere annealing furnace and subjected to the following time-temperature programme:

| | | |
|---|---|---|
| 6 h | 25–300 DEG C. | pulsating argon (1,000/1,500 mbar) |
| 2 h | 300–780 DEG C. | pulsating argon (30/10 mbar) |
| 10 h | 780 DEG C. | pulsating argon (30/10 mbar) |
| 2 h | 780–1,100 DEG C. | pulsating argon (30/10 mbar) |
| 5 h | 1,100 DEG C. | pulsating argon (30/10 mbar) |

During a first heating-up to a temperature of 300 DEG C, the water and the organic binder were eliminated. In this process, titanium hydride turned out to be chemically totally inert with respect to water and the binder. This is in line with the findings taught in specialised literature, where it is described that titanium hydride—as long as during its decomposition it releases greater quantities of hydrogen—is totally protected against the intrusion of external gases. Under the test conditions described above, the decomposition of titanium hydride starts slightly below 600 DEG C and is largely finished at 780 DEG C. At the same time, the sintering process starts at the contact points of the freshly formed titanium particles. The temperature was stabilised at 780 DEG C, as this temperature is slightly inferior to the melting temperature of sodium chloride (801 DEG C), so that the structure may be exposed to the sintering process for 10 hours without shrinkage.

Subsequently, the temperature was increased to 1,100 DEG C for two hours, during which the sodium chloride melted and mostly ran out of the shaped body. During the following five hours, the greatest part of the remaining sodium chloride evaporated, and simultaneously a linear shrinkage of 18 percent was observed, which, however, was effective in a uniform manner in all directions. Almost completely freed of sodium chloride, the shaped body was subsequently rinsed for several hours in running water. The result was a structure with a degree of porosity of 79.5 percent by volume provided with interconnecting pores having a medium pore size of 0.62 mm which were evenly distributed in an arrangement approximately resembling a densest sphere packing. Mechanical trials showed that this structure was characterised by a considerable degree of brittleness, which indicated that the content of oxygen dissolved in the titanium was too high. This results from the high reactivity of the titanium, i.e. even small amounts of impurities present in the titanium hydride, which on its surface contains thin layers of oxide, may be sufficient for bringing about this deterioration of the mechanical properties, since a shaped body of this type comprises a huge internal surface area. According to claim 17, the shaped body, placed together with calcium granulate in an evacuated, thin-walled steel retort, was inserted into the protective atmosphere-furnace and exposed to a temperature of 1,000 DEG C during 4 hours. The calcium steam pressure produced during this process created a deep oxidation potential on the inner surface areas of the shaped body so that the oxygen by way of solid state diffusion diffused from the thin cell walls towards the outside where it reacted with the steam to form calcium oxide. After this treatment the shaped body was equally washed with diluted hydrochloric acid, and this titanium body displayed an excellent tenacity behaviour.

EXAMPLE 4

A fourth example shows a case in which a solid titanium component is coated with a surface layer made of porous titanium. For this purpose, fine calcium fluoride particles were agglomerated with an alginate to form balls having a diameter of 0.5 mm. These balls were subsequently mixed with a mixture consisting of 90 percent by mass of pure titanium powder having a medium particle size of 15 $\mu$m and 10 percent by mass of titanium hydride, adding an alcohol/wax mixture, and stirred to a viscid paste. Subsequently, this paste was manually applied on the electrode to form a layer having a thickness of approximately 3 mm and dried during 48 hours in the drying cabinet at 110 DEG C. Subsequently, the following temperature-time programme was run:

| | | |
|---|---|---|
| 6 h | 25–300 DEG C. | pulsating argon (1,000/1,500 mbar) |
| 2 h | 300–1,250 DEG C. | pulsating argon (30/10 mbar) |
| 2 h | 1,250 DEG C. | pulsating argon (30/10 mbar) |

Since calcium fluoride melts only at temperatures beyond 1,400 DEG C, the particles remained inside the shaped body and, therefore, had to be eliminated subsequent to the sintering process by means of a chemical solution. At this point, the advantage became evident which resides in the fact that the calcium fluoride particles had previously been agglomerated into spherical bodies based on much finer powder particles. Once the alginate had disintegrated at temperatures of below 300 DEG C, the remaining, loosely arranged masses of calcium fluoride particles were kept in place by the titanium particles and titanium hydride particles surrounding them. However, as soon as the sintering process of the titanium phase started, which in this example took place more rapidly and at considerably higher temperatures, the loosely arranged calcium particle masses were exposed to a compressive force and thus prevented the surface tension from causing a strong shrinkage of the structure. Subsequent to the sintering process, the cooled-down titanium body was rinsed in a well-stirred complexone solution during several days in the course of which the calcium fluoride particles were slowly dissolved.

What is claimed is:

1. A mixture of two particulate phases to be used in the production of a green compact for sintering at higher temperatures, wherein
   A) a first phase contains particles that consist of a metal compound, comprising hydrides of at least one metal that forms a sintered alloy;
   B) a second phase contains particles selected from a group of inorganic compounds, which at temperatures beyond 400° C., do not release any decomposition products that are interstitially soluble in the sintering metal phase and/or react with said phase to form stable compounds; and
   C) that the inorganic compounds are selected from a group consisting of alkali halogenides and alkaline earth halogenides.

2. The mixture as claimed in claim 1, wherein the metal compound is a titanium compound.

3. The mixture as claimed in claim 1, wherein the first phase of the mixture additionally comprises particles that consist of a metal.

4. The mixture as claimed in claim 1, wherein the first phase of the mixture additionally comprises particles that consist of a metal alloy.

5. The mixture as claimed in claim 1, wherein the inorganic compounds are selected from the following group consisting of: NaCl, $CaF_2$, $K_3AlF_6$ and $Na_3AlF_6$.

6. The mixture as claimed in claim 1, wherein the bodies of the first and/or the second phase are agglomerates or shaped corpuscles of powder particles that are kept in place by a binder that disintegrates and/or evaporates at temperatures below a beginning of a sintering process.

7. The mixture as claimed in claim 1, wherein the first phase comprises oxides of at least one of the metals that form the sintered alloy.

8. The mixture as claimed in claim 1, wherein the first phase comprises nitrides of at least one of the metals that form the sintered alloy.

9. The mixture as claimed in claim 1, wherein the first phase comprises particles consisting of titanium hydride.

10. The mixture as claimed in claim 1, wherein at least part of the particles of the first phase are provided with a metal coating which in contact with the other components of the first phase form, at least at the beginning of a sintering process, a low melting point alloy and that after termination of the sintering process the concentration of this metal in the alloy corresponds to the desired value.

11. The mixture as claimed in claim 1, wherein, in addition to the first and second phases, the mixture further comprises a third phase, sid third phase comprising an organic or inorganic binder in a composition corresponding to that used in powder injection molding.

12. A method for producing a shaped body claimed in claim 1, comprising the steps of mixing the first and second phases together to form a homogeneous mixture and inserting said mixture into a mold which, at a sintering temperature, is thermally and chemically stable, and sintering the mixture to form a shaped body.

13. A shaped body which is obtained by the method according to claim 12.

14. A method for producing shaped metal bodies with interconnecting pore structures by using the shaped body as claimed in claim 13, comprising a sintering process of heating of the green compact until the particles of the first phase are sintered so as to form an interconnecting pore structure, and eliminating the particles of the second phase from the pores of the shaped body during or subsequent to the sintering process.

15. The method as claimed in claim 14, wherein the elimination of the particles of the second phase takes place prior to or during the sintering process at a temperature beyond 400° C.

16. The method as claimed in claim 15, wherein the elimination of the particles of the second phase takes place subsequent to the sintering process by dissolving out said particles using a solvent.

17. The method as claimed in claim 16 wherein after having undergone the sintering process, the shaped body is treated with a liquid and/or a vaporous alkali metal or alkaline earth metal.

18. A shaped metal body obtained in accordance with the method of claim 17.

19. The shaped metal body as claimed in claim 18, wherein the pores of the interconnecting pore structure have a diameter smaller than 0.4 mm.

20. The shaped metal body as claimed in claim 18, wherein the shaped metal body is one of a surgical implant and a coating for a surgical implant.

21. The shaped metal body as claimed in claim 18, wherein the shaped metal body is a structural member for applications in lightweight construction.

22. The shaped metal body as claimed in claim 18, wherein the shaped metal body is an electrode material.

* * * * *